(12) United States Patent
Sun et al.

(10) Patent No.: US 10,893,942 B2
(45) Date of Patent: Jan. 19, 2021

(54) OFFSET ADAPTER UNIT

(71) Applicant: CORENTEC CO., LTD., Cheonan-si (KR)

(72) Inventors: Doo-Hun Sun, Seoul (KR); Goon-Hee Lee, Seoul (KR); Oui-Sik Yoo, Seoul (KR); Jung-Woo Seo, Seoul (KR); Yeo-Kyung Kang, Seoul (KR)

(73) Assignee: Corentec Co., Ltd., Cheonan-si (KR)

( * ) Notice: Subject to any disclaimer, the term of this patent is extended or adjusted under 35 U.S.C. 154(b) by 143 days.

(21) Appl. No.: 15/535,835

(22) PCT Filed: Nov. 24, 2015

(86) PCT No.: PCT/KR2015/012608
§ 371 (c)(1),
(2) Date: Jun. 14, 2017

(87) PCT Pub. No.: WO2016/099041
PCT Pub. Date: Jun. 23, 2016

(65) Prior Publication Data
US 2017/0348105 A1 Dec. 7, 2017

(30) Foreign Application Priority Data

Dec. 18, 2014 (KR) .................. 10-2014-0183136

(51) Int. Cl.
*A61F 2/46* (2006.01)
*A61F 2/30* (2006.01)
*A61F 2/38* (2006.01)

(52) U.S. Cl.
CPC .......... *A61F 2/30734* (2013.01); *A61F 2/389* (2013.01); *A61F 2/3859* (2013.01);
(Continued)

(58) Field of Classification Search
CPC ............ A61F 2/389; A61F 2002/30736; A61F 2002/30878; A61F 2/30721; A61F 2/3859;
(Continued)

(56) References Cited

U.S. PATENT DOCUMENTS 5,330,535 A * 7/1994 Moser ................. A61F 2/30721
623/20.35
5,415,659 A * 5/1995 Lee .................... A61B 17/7007
24/569

(Continued)

FOREIGN PATENT DOCUMENTS

JP 5448842 B2 3/2014

OTHER PUBLICATIONS

International Search Report dated Mar. 2, 2016, issued in PCT Application No. PCT/KR2015/012608, filed Nov. 24, 2015.
(Continued)

*Primary Examiner* — Ann Schillinger
(74) *Attorney, Agent, or Firm* — Workman Nydegger

(57) ABSTRACT

The present invention relates to an implant playing a role as a joint in coupling a revision implant in revision total knee arthroplasty and, more specifically, to an offset adapter unit comprising an adapter which couples a femoral member or a tibial member to a stem member in revision total knee arthroplasty; and a nut coupled to the adapter, thereby improving the strength by considering fracture occurring in the narrowest area.

8 Claims, 8 Drawing Sheets

(52) U.S. Cl.
CPC .............. *A61F 2002/3054* (2013.01); *A61F 2002/3069* (2013.01); *A61F 2002/30405* (2013.01); *A61F 2002/30411* (2013.01); *A61F 2002/30507* (2013.01); *A61F 2002/30555* (2013.01); *A61F 2002/30736* (2013.01); *A61F 2002/30878* (2013.01)

(58) Field of Classification Search
CPC ............ A61F 2/385; A61F 2002/30332; A61F 2220/0025; A61F 2/30734; A61F 2002/30344; A61F 2002/30405; A61F 2002/30507
See application file for complete search history.

(56) References Cited

U.S. PATENT DOCUMENTS

| | | | |
|---|---|---|---|
| 5,653,765 A | 8/1997 | Mctighe | |
| 6,171,342 B1 | 1/2001 | O'Neil | |
| 8,308,772 B2 * | 11/2012 | Clement | ............ A61B 17/7037 606/267 |
| 8,540,775 B2 | 9/2013 | Reich | |
| 2008/0167722 A1 * | 7/2008 | Metzger | .............. A61F 2/30721 623/20.36 |
| 2009/0117520 A1 * | 5/2009 | Kikuchi | ................. A61C 8/005 433/174 |
| 2009/0149963 A1 | 6/2009 | Sekel | |

OTHER PUBLICATIONS

Written Opinion dated Mar. 2, 2016, issued in PCT Application No. PCT/KR2015/012608, filed Nov. 24, 2015.

* cited by examiner

OFFSET ADAPTER UNIT

TECHNICAL FIELD

The present invention relates to an implant playing a role as a joint in coupling a revision implant in revision total knee arthroplasty and, more specifically, to an offset adapter unit comprising an adapter which couples a femoral member or a tibial member to a stem member in revision total knee arthroplasty; and a nut coupled to the adapter, thereby improving the strength by taking into consideration fracture occurring in the narrowest area.

BACKGROUND

There are joints, being parts connecting bones and capable of freely moving, in a human body. Of the joints, the largest joint is the knee joint. The knee joint is disposed in a middle part of a leg and consists of a tibiofemoral joint and a patellofemoral joint.

The knee joint replacement surgery is performed when there is trouble walking or discomfort in daily activities due to severe pain in the knee joint and degenerative arthritis. However, even after surgery there can be a case where pain occurs again and walking becomes problematic as time passes. Then reoperation may be done after diagnosis, which is called revision total knee arthroplasty.

However, it is difficult to firmly fix an artificial joint in the revision total knee arthroplasty, unlike in the knee joint replacement surgery, because of lack of strong bones as bones around the artificial joint had already been melted at the time of the revision total knee arthroplasty. Thus, fixing force of a replacement should be reinforced by attaching an extension stem to the artificial joint. The diameter and the length can be adjusted based on size and length of the tibia and the femur. The extension stem is configured to be detachable from a main body and is fixed by twisting and tightening. Often, the extension stem is not formed straightly or the extension stem is attached to a location off-center of the replacement in preparation for a case where bone defects are irregular or bone deformities are severe. This is called off-center or offset.

Referring to FIGS. 1 and 2, an offset adapter unit according to prior art is described. The prior adapter unit comprises an adapter 100 and a nut 200, and the prior adapter 100 includes a head portion 110 being an upper feature and a body portion 120 being a lower feature. The head portion 110 includes a screw groove 111a having a center axis A1. Also, the body portion 120 is eccentric to the head portion 110 and includes a screw portion 122a having a diameter D and a center axis A2. However, there is a problem of increasing pain in patients and risk of reoperation due to a fractured neck 150 caused by repetitive bending moments which occur due to axial loads applied vertically when a common offset is connected and fixed to the femur or tibia.

(Prior Art) Korean Patent Application Publication No. 10-1989-0019611 Modular Knee Prosthesis System

DETAILED DESCRIPTION

Technical Problem

The present invention has been made in an effort to solve the problems.

An object of the present invention is to provide an offset adapter unit which prevents fracture in the narrowest part (neck) by generating an expanded step in a screw connecting region of an adapter for resolving the most vulnerable part to continuously occurring bending moments.

Another object of the present invention is to provide an offset adapter unit which prevents fracture in the narrowest part (neck) by covering the adapter with a nut having a step.

Technical Solutions

In order to achieve the above object, the present invention is realized by embodiments having the following features.

According to one embodiment of the present invention, an offset adapter unit comprises: an adapter which couples a femoral member or a tibial member to a stem member in revision total knee anthroplasty.

According to another embodiment of the present invention, in the offset adapter unit, the adapter comprises: a head portion; and a body portion.

According to still another embodiment of the present invention, in the offset adapter unit, the head portion includes a screw groove capable of coupling to the stem member.

According to still another embodiment of the present invention, in the offset adapter unit, the body portion comprises: an expanded portion and a screw portion.

According to still another embodiment of the present invention, in the offset adapter unit, the expanded portion forms a step in a direction of the body portion from the head portion.

According to still another embodiment of the present invention, in the offset adapter unit, the screw portion is formed as a male screw to be coupled to the femoral member or the tibial member.

According to still another embodiment of the present invention, the offset adapter unit further comprises a nut coupled to the adapter.

According to still another embodiment of the present invention, in the offset adapter unit, the nut comprises: a step portion and a female screw portion.

According to still another embodiment of the present invention, in the offset adapter unit, the step portion is coupled to the expanded portion by contact.

According to still another embodiment of the present invention, in the offset adapter unit, the female screw portion is coupled to a part of the screw portion of the adapter.

Advantageous Effects

According to the above-described embodiments and the following features, combinations, and relations of use that will be described later, the present invention can obtain the following effects.

The present invention provides an offset adapter unit which prevents fracture in the narrowest part (neck) by generating an expanded step in a screw connecting region of an adapter for resolving the most vulnerable part to continuously occurring bending moments.

The present invention provides an offset adapter unit which prevents fracture in the narrowest part (neck) by covering the adapter with a nut having a step.

BEST MODE

Hereinafter, exemplary embodiments of an offset adapter unit according to the present invention will be described with reference to the accompanying drawings. In describing the present invention, unless not specifically defined, all terminologies in the specification should be interpreted based on the general meanings thereof that a person skilled in the art understands. When the general meanings of the terminologies are incompliant with those used in the specification, the terminologies should be interpreted as being defined herein. Also, well-known functions or constructions will not be described in detail in case they may unnecessarily obscure the understanding of the present invention.

Figure 3:
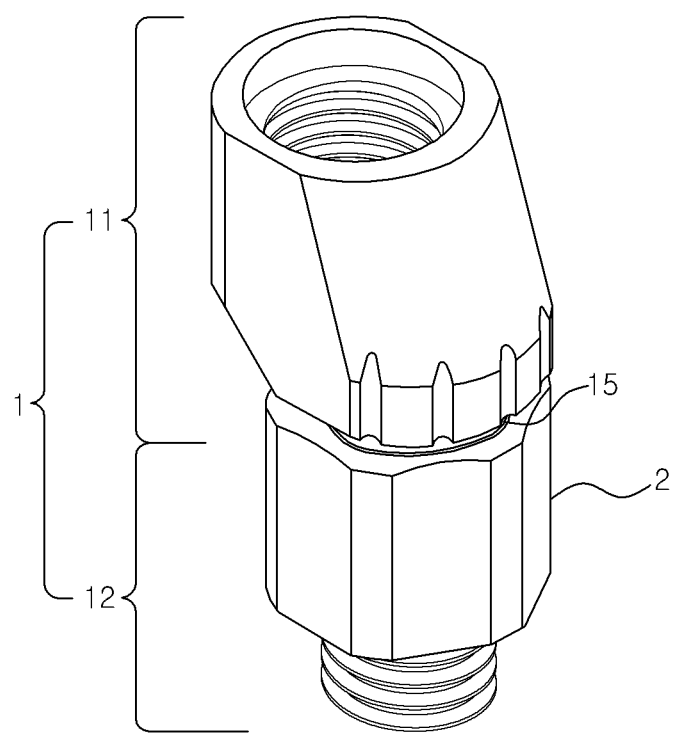
FIG. 3 is an engaged perspective view of an offset adapter unit according to the present invention.
Figure 4:
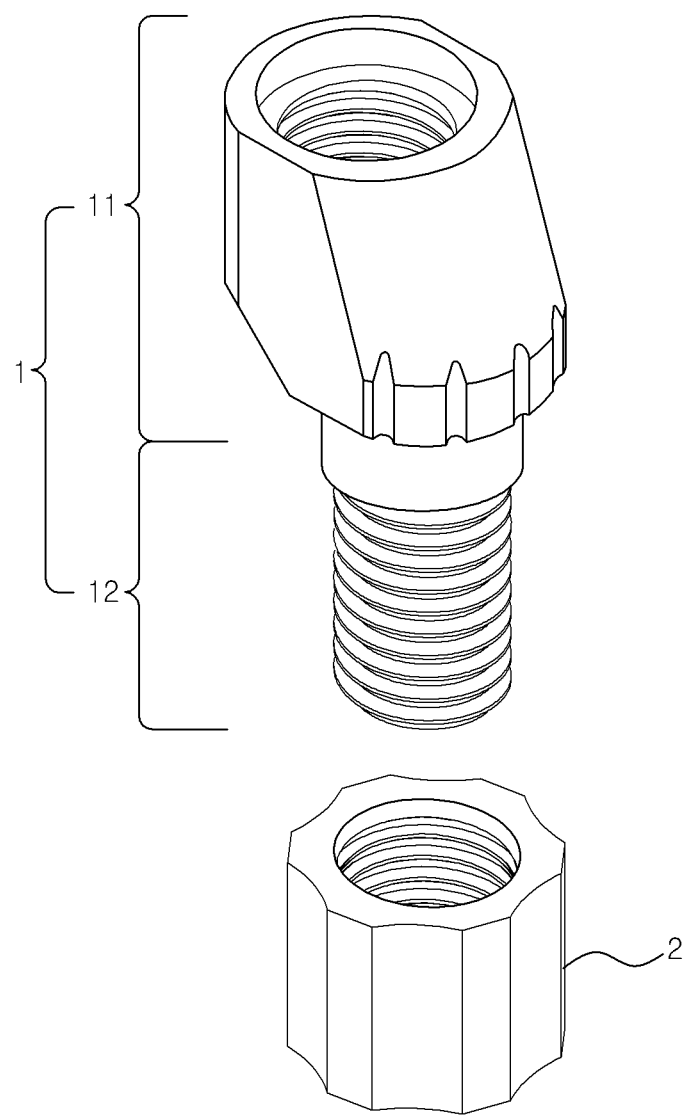
FIG. 4 is an exploded perspective view of the offset adapter unit according to the present invention.
Figure 5:
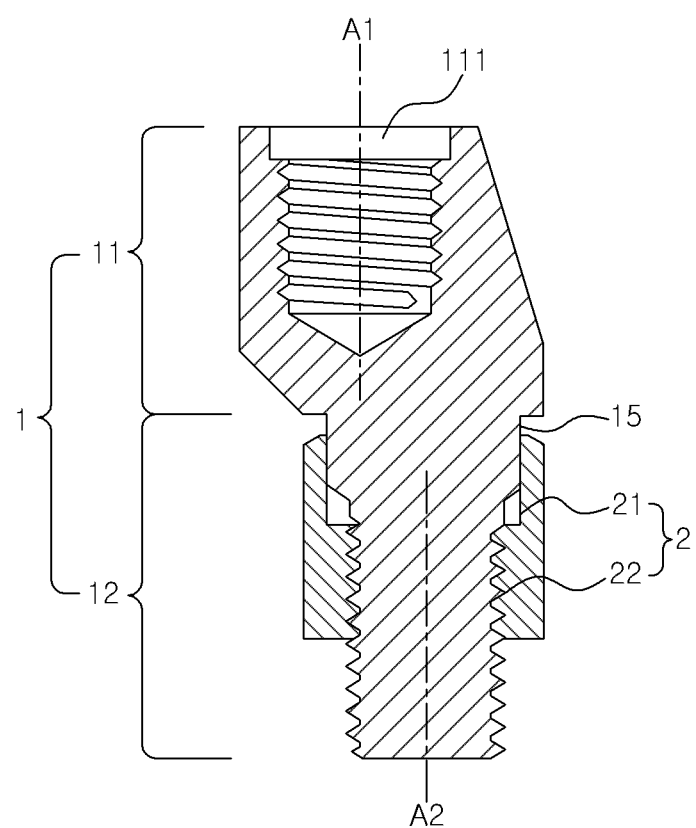
FIG. 5 is an engaged sectional view of the offset adapter unit according to the present invention.
Figure 6:
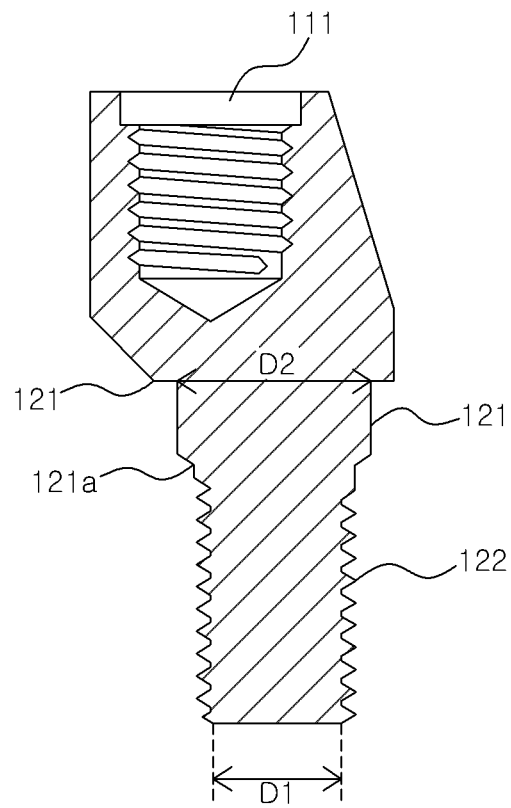
FIG. 6 is a sectional view of the offset adapter unit according to the present invention.
Figure 7:
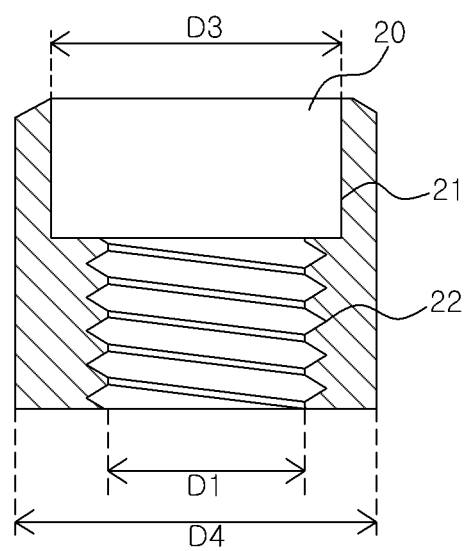
FIG. 7 is a sectional view of the nut of the offset adapter unit according to the present invention.
Figure 8:
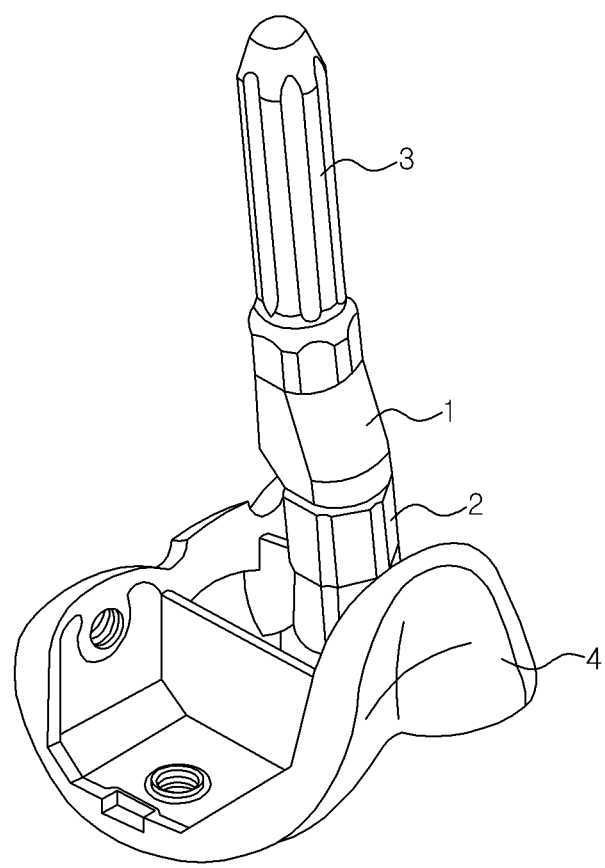
FIG. 8 is an engaged perspective view of a stem member, a femoral member of and the offset adapter unit according to the present invention.

FIG. 3 is an engaged perspective view of an offset adapter unit according to the present invention; FIG. 4 is an exploded perspective view of an adapter and a nut of the offset adapter unit according to the present invention; FIG. 5 is an engaged sectional view of the offset adapter unit according to the present invention; FIG. 6 is a sectional view of the offset adapter unit according to the present invention; FIG. 7 is a sectional view of the nut of the offset adapter unit according to the present invention; FIG. 8 is an engaged perspective view of a stem member, a femoral member, and the offset adapter unit according to the present invention; and FIG. 9 is an engaged perspective view of a stem member, a tibial member and the offset adapter unit according to the present invention.

With reference to FIGS. 3 to 9, the offset adapter unit according to one embodiment of the present invention is described. For resolving a portion which is the most vulnerable to bending moments which continuously occur, the offset adapter unit produces an expanded portion 121 in a screw connecting region of an adapter 1 and a nut 2 having a step portion 21 covers the adapter 1 to prevent fracture of a neck 15 being the narrowest portion.

Figure 9:
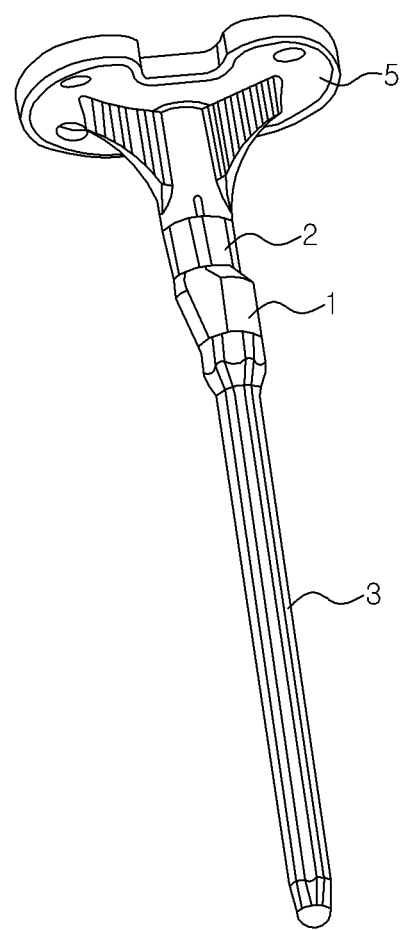
FIG. 9 is an engaged perspective view of a stem member, a tibial member and the offset adapter unit according to the present invention.

Referring to FIGS. 8 to 9, the offset adapter unit couples a stem member 3 to a femoral member 4 or a tibial member 5 in revision knee arthroplasty and comprises the adapter 1 and the nut 2.

Referring to FIG. 4, the adapter 1 comprises a head portion 11 being an upper structure and a body portion 12 being a lower structure.

Referring to FIG. 5, the head portion 11 comprises a screw thread 111 having a center axis A1. The screw groove 111 has a female screw thread along an inner circumferential face and the pitch, angle, diameter, number and the like of the thread are formed dependent on a male screw of the stem member 3.

Referring to FIGS. 5 and 6, the body portion 12 is eccentric to the head portion 11 and formed around A2 as a center axis. The body portion 12 comprises the expanded portion 121 formed by decreasing the diameter of a lower face 112 of the head portion 11 and extending downward; and the screw portion 122 formed by decreasing the diameter of a lower face 121a of the expanded portion 121.

Referring to FIG. 6, the expanded portion 121 of the diameter D2 formed by decreasing the diameter of and extending downward from the lower face 112 of the head portion 11 is formed to prevent fracture of the neck 15 vulnerable to the continuously occurring bending moments.

The screw portion 122 forms a diameter D1 by decreasing the diameter of the lower face 121a of the expanded portion 121 and includes a male screw thread in an outer surface of the screw portion 122.

Referring to FIGS. 6, 8 and 9, the screw portion 122 of the adapter 1 is formed as a male screw thread to couple to the femoral member 4 or the tibial member 5 for coupling with the femoral member 4 or the tibial member 5 including a female screw thread. The pitch, angle, diameter, number and the like of the thread of the screw portion 122 are formed dependent on the female screw of the femoral member 4 or the tibial member 5.

Referring to FIG. 7, the outer diameter of the nut 2 is formed by D4 and the nut 2 includes a penetration hole 20 which penetrates therethrough. In addition, the penetration hole 20 is formed by being surrounded by the step portion 21 which makes contact with the expanded portion 121 of the adapter 1 and the female screw portion 22 coupled to the body portion 12 of the adapter 1 when the nut 2 is fastened to the adapter 1.

Referring to FIG. 7, the step portion 21 is a part which contacts with the expanded portion 121 when the nut 2 is fastened to the adapter 1. The step portion 21 is formed with an inner diameter of D3 in an upper portion of the nut 2. Also, the step portion 21 is configured to prevent fracture of the neck 15 which is the narrowest part by covering the expanded portion 121 of the adapter 1 when the adapter 1 is fastened to the nut 2.

Referring to FIG. 7, the female screw portion 22 is a part which contacts with the screw portion 122 when the adapter 1 is fastened to the nut 2. The female screw portion 22 is formed in a lower end of the step portion 21 with an inner diameter of D1 decreased from the step portion 21. Also, the female screw portion 22 is configured to unite the adapter 1 and the nut 2 when the adapter 1 is fastened to the nut 2 and includes screw threads in an inner circumferential face.

Referring to FIGS. 6 and 7, the diameter D2 of the expanded portion 121 is greater than the diameter D1 of the screw portion 122, and the diameter D1 of the screw portion 122 is approximately the same with the diameter D2 of the female screw portion. Also, the diameter D3 of the step portion 21 is greater than or equal to the diameter D2 of the expanded portion 12. The outer diameter D4 of the nut 2 is greater than the diameter D3 of the step portion 21. Hence, the diameters are formed to have a relationship of D4≥D3≥D2≥D1.

Referring to FIG. 8, the femoral member 4 is coupled to the body portion 12 of the adapter 1 and the stem member 3 is coupled to the head portion 11 of the adapter 1. The femoral member 4 is configured to be fixed by the nut 2 after an axis of the femoral member 4 is adjusted when being fastened to the nut 2 in order to adjust an offset to the femur of a patient.

Referring to FIG. 9, the tibial member 5 is coupled to the body portion 12 of the adapter 1 and the stem member 3 is coupled to the head portion 11 of the adapter 1. The tibial member 5 is configured to be fixed by the nut 2 after an axis of the tibial member 5 is adjusted when being fastened to the nut 2 in order to adjust an offset to the tibial of the patient.

Figure 1:
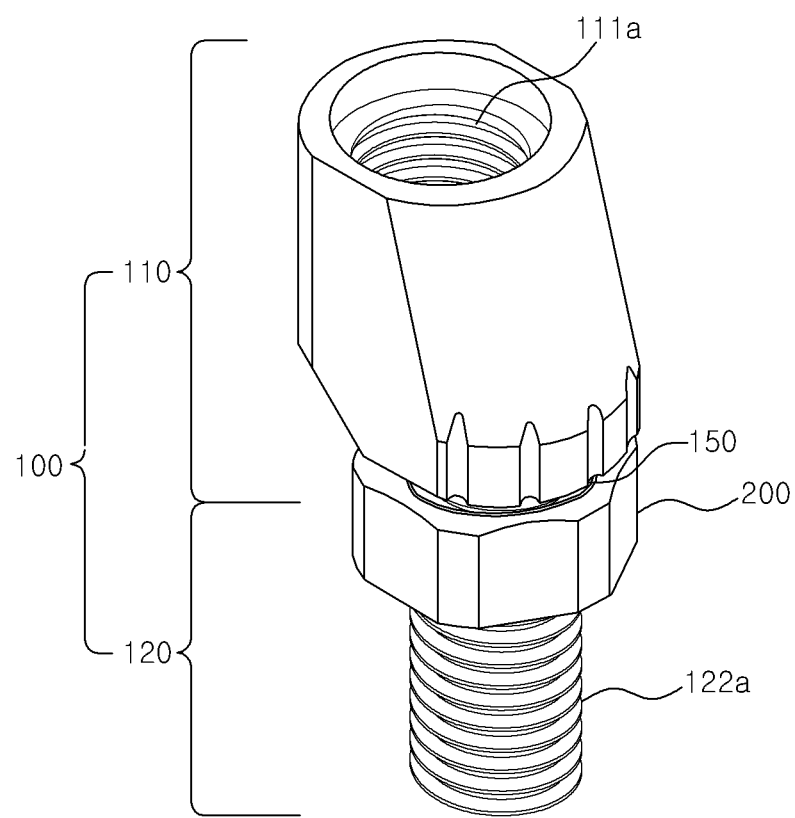
FIG. 1 is an engaged perspective view of an offset adapter unit according to prior art.
Figure 2:
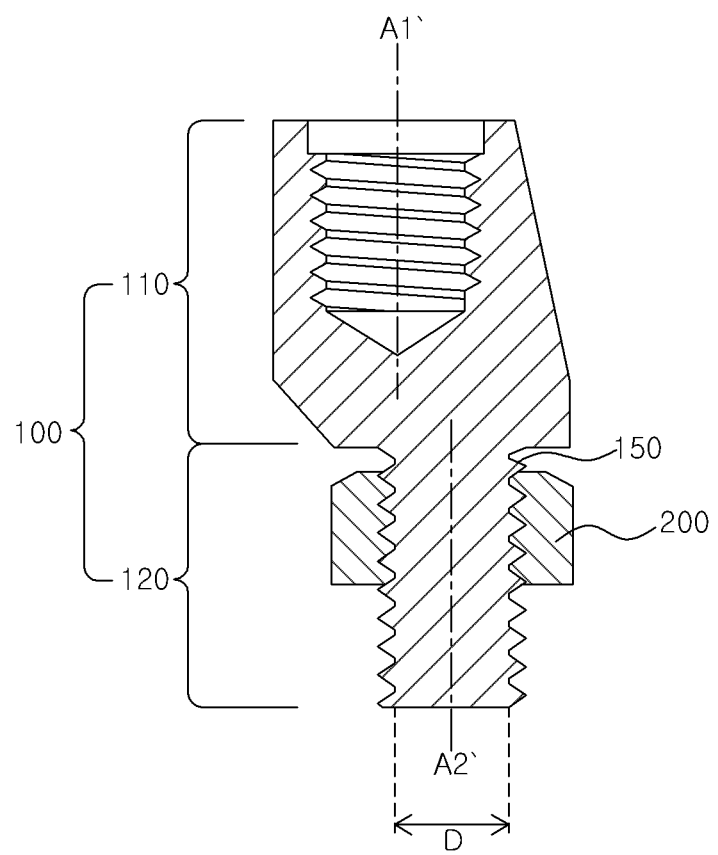
FIG. 2 is an engaged section view of the offset adapter unit according to prior art.

Referring to FIGS. 2 and 5, the body portion 120 of the prior adapter 100 extends from the upper portion to the lower portion with a constant diameter D, which causes fracture in the neck 150 subjected to repetitive bending moment due to eccentricity of the axis when being fastened to the nut 200. On the other hand, according to the present invention, the expanded portion 121 is formed in the adapter 1, and the overall diameter of the neck 15 being the weak part is made larger by enabling the step portion 21 of the nut 2 to cover the expanded portion 121. Accordingly, the strength of the adapter unit according to the present invention is greatly improved compared to the prior art.

In the above, the applicant described preferred embodiments of the present invention. It should be interpreted that such embodiments are merely examples which implement the technical idea and any modification or revision falls within the scope of the prevent invention if it implements the technical idea of the present invention, however.

The invention claimed is:

1. An offset adapter unit for use in coupling a femoral member or a tibial member to a stem member in a total knee arthroplasty revision, the offset adapter unit comprising:
   an adapter comprising:
      a head, comprising:
         a female screw groove extending at least partially into the head through a top surface of the head; and
         a lower surface having a first diameter;
      a body extending from the head, the body and the head being a single, integral, unitary, and monolithic structure, the body comprising:
         an upper expanded portion extending from the lower surface of the head, the upper expanded portion having a second diameter that is less than the first diameter; and
         a lower screw portion extending monolithically from a lower surface of the upper expanded portion, the lower screw portion having a third diameter that is less than the second diameter and wherein the lower screw portion is threaded; and
   a nut, comprising:
      a lower female screw portion having an inside surface that directly engages the threads of the lower screw portion of the body during use; and
      an upper step portion having an inside surface that contacts the upper expanded portion of the body during use, the upper step portion extending from the lower female screw portion, the upper step portion and the lower female screw portion being a single, integral, unitary, and monolithic structure.

2. The offset adapter unit of claim 1, wherein the upper step portion has a first inner diameter that is equal to the second diameter.

3. The offset adapter unit of claim 2, wherein the lower female screw portion of the nut has a second inner diameter that is less than the first inner diameter of the upper step portion of the nut.

4. An arthroplasty revision offset adapter unit, the offset adapter unit comprising:
   an adapter comprising:
      a head comprising a lower surface having a first diameter;
      a body extending monolithically from the head, comprising:
         an upper expanded portion extending from the lower surface of the head, the upper expanded portion having a second diameter; and
         a lower screw portion extending monolithically from a lower surface of the upper expanded portion, the lower screw portion having a third diameter that is less than the second diameter; and
   a nut, comprising:
      a lower female screw portion that directly engages the lower screw portion of the body; and
      an upper step portion having an inside surface that at least partially surrounds and contacts the upper expanded portion of the body, the upper step portion extending monolithically from the lower female screw portion.

5. The offset adapter unit of claim 4, wherein the second diameter of the upper expanded portion of the body is less than the first diameter of the lower surface of the head.

6. The offset adapter unit of claim 4, the head further comprising a female screw groove extending at least partially into the head through an upper surface of the head.

7. The offset adapter unit of claim 6, wherein the female screw groove has a first central axis that is offset from a second central axis of the lower screw portion of the body.

8. An arthroplasty revision offset adapter unit, the offset adapter unit comprising:
   an adapter comprising:
      a head, comprising:
         a female-threaded screw groove extending at least partially into the head through a top surface of the head; and
         a lower surface having a first diameter;
      a body extending from the head, the body comprising:
         an upper expanded portion extending from the lower surface of the head, the upper expanded portion having a lower portion having a second diameter; and
         a lower screw portion extending from the lower portion of the upper expanded portion, the lower screw portion having a third diameter that is less than the second diameter; and
   a nut, comprising:
      a lower female screw portion that directly engages the lower screw portion of the body; and
      an upper step portion having an inside surface that at least partially surrounds and contacts the upper expanded portion of the body
   wherein the female-threaded screw groove has a first central axis that is parallel to and offset from a second central axis of the lower screw portion of the body.

* * * * *